United States Patent [19]

Poutsma et al.

[11] 4,119,656

[45] Oct. 10, 1978

[54] PREPARATION OF HYDROXYLATED COMPOUNDS FROM SYNTHESIS OF GAS WITH PALLADIUM CATALYSTS

[75] Inventors: Marvin Lloyd Poutsma, Ossining; Jule Anthony Rabo, Armonk; Alan Peter Risch, Garnersville, all of N.Y.

[73] Assignee: Union Carbide Corporation, New York, N.Y.

[21] Appl. No.: 797,242

[22] Filed: May 16, 1977

Related U.S. Application Data

[63] Continuation of Ser. No. 638,304, Dec. 8, 1975, abandoned.

[51] Int. Cl.² ............................................. C07C 27/06
[52] U.S. Cl. .............................. 260/449 R; 260/449.5
[58] Field of Search ....................... 260/449 R, 449.5; 638/304

[56] References Cited

U.S. PATENT DOCUMENTS 1,681,753   8/1928   Storch ............................... 260/449.5

FOREIGN PATENT DOCUMENTS 824,822   7/1975   Belgium ................................... 260/449

OTHER PUBLICATIONS

Aben, Journal of Catalysis 10 224–229, 1968.
Kratel, Uber die Ergnung der Edelmuttalle als Katalysatoren zur Kohlenagd Reductin (Bensum synthese) unter Druck, Thesis 1937 U. of Berlin Charlottenburg, 59–62.

*Primary Examiner*—Howard T. Mars
*Attorney, Agent, or Firm*—Bernard Lieberman

[57] ABSTRACT

A heterogeneous catalytic process for producing hydroxylated hydrocarbons containing from 1-2 carbon atoms which comprises: contacting a synthesis gas containing carbon monoxide and hydrogen with a catalyst consisting essentially of palladium at reaction conditions such that hydroxylated compounds are selectively produced while substantially avoiding the concomitant formation of methane or higher molecular weight hydrocarbons.

5 Claims, No Drawings

PREPARATION OF HYDROXYLATED COMPOUNDS FROM SYNTHESIS OF GAS WITH PALLADIUM CATALYSTS

This application is a continuation of our prior U.S. application Ser. No. 638,304 filing date Dec. 8, 1975 abandoned.

This invention relates, in general, to the selective formation of one and two-carbon atom hydroxylated hydrocarbons from synthesis gas. More particularly, the invention concerns reacting synthesis gas in the presence of a palladium catalyst to form methanol and other hydroxylated compounds while substantially avoiding the concomitant formation of hydrocarbons such as methane.

The formation of a wide spectrum of products comprising hydrocarbons and oxygenated compounds is a characteristic of most synthesis from a CO and $H_2$ mixture. In today's marketplace, most oxygenated compounds have greater commercial value than hydrocarbons. Consequently, it is a desired objective to be able to selectively produce only commercially valuable oxygenated products in a synthesis gas process while minimizing the formation of hydrocarbon by-products.

The use of reaction catalysts to influence the product distribution resulting from the hydrogenation of carbon monoxide is well known in the art. Thus, for example, oxides and mixed oxides of metals such as zinc, chromium and copper are known to be effective catalysts for producing methanol from synthesis gas. Similarly, certain of the Group VIII metals of the Periodic Table such as, iron, cobalt, nickel and ruthenium are effective catalysts for the production of predominantly hydrocarbons. Two recent studies of palladium, a Group VIII metal, have shown it to be a selective methanation catalyst, [see, M. A. Vannice, Journal catalysis, vol. 37, pages 449 and 462, (1975); and Mills et al, Catalysis Review, vol. 8, page 159 (1973)]. Palladium has also been disclosed as a dopant in conjunction with methanol forming catalysts. Thus, in Kinetics Catalysis, vol. 10, page 859 (1969), there is disclosed a mixed oxide catalyst of zinc and chromium which is doped with palladium to promote dissociative chemisoption of hydrogen, thereby improving the selectivity of the synthesis gas reaction to methanol. Further, in German Pat. No. 293,787, issued in 1913, palladium is listed among nine other metals as being useful for producing a mixture of hydrocarbons, alcohols, ketones, aldehydes and acids for synthesis gas.

The aforementioned German Patent No. 293,787 has been characterized in a scientific paper [Bull. Acad. Sci. USSR, Div. Chem. Sci. No. 7, page 1129 (1965)] as being representative of old patent data which discloses the use of palladium to form complex mixtures of oxygenated products with a small admixture of hydrocarbons from carbon monoxide and hydrogen. However, in a more detailed investigation of palladium as a catalyst for this purpose, [R. Kratel, "Concerning the Suitability of Noble Metals as Catalysts for Carbon Monoxide Reduction (Gasoline Synthesis) under Pressure," Thesis, University of Berlin-Charlottenburg, 1973] it was concluded that of all the noble metals, palladium catalyzes the reduction of carbon monoxide under pressure least effectively. Moreover, the teachings of the aforementioned German Patent were specifically refuted. Specifically, the following was stated on page 62 of the above-mentioned Kratel Thesis: "Liquid hydrocarbons and oxygen-containing compounds as was described in German Pat. No. 293,787 could not be demonstrated on palladium."

Accordingly, the use of palladium in the prior art has been restricted to either functioning as a dopant in conjunction with traditional methanol forming catalysts, such as zinc and chromium oxides, or to being considered marginally useful for producing a wide spectrum of oxygenated and non-oxygenated products. Consequently, the prior art has not contemplated using palladium as a catalyst in its own right to selectively form 1-2 carbon atom hydroxylated compounds, such as methanol and ethylene glycol, to the exclusion of hydrocarbons.

SUMMARY

In accordance with the invention, a heterogeneous catalytic process is provided for producing hydroxylated hydrocarbons containing from 1-2 carbon atoms which comprises contacting a synthesis gas containing carbon monoxide and hydrogen with a catalyst consisting essentially of palladium at reaction conditions such that oxygenated organic compounds are selectively produced while substantially avoiding the concomitant formation of methane or higher molecular weight hydrocarbons.

Useful hydroxylated organic compounds, in particular methanol, are produced in accordance with the invention at temperatures between about 200° and about 400° C. correlated with pressures between about 150 and about 20,000 psia. The preferred reactive conditions are a temperature between about 260° and about 350° C. and a pressure between about 150 and 3,000 psia. In addition to methanol, the synthesis reaction typically produces lesser amounts of hydroxylated compounds such as, ethanol, and ethylene glycol, and still lesser amounts of propylene glycol, and butanediols. Methyl formate is also produced in small quantities. An important characteristic of the invention is the high selectivity of the process with respect to forming hydroxylated compounds. Thus, 1-2 carbon atom hydroxylated compounds are produced in accordance with the invention in quantities greater than 90%, by weight, of the total product mixture, and more typically, greater than 97%, by weight, of the product mixture. The production of methane and other hydrocarbons is substantially avoided to the extent that the concentration of by-product hydrocarbons is less than about 1%, by weight, of the total product mixture, and frequently is present only in trace amounts.

DETAILED DESCRIPTION

In accordance with the invention, a synthesis gas containing carbon monoxide and hydrogen is contacted with a solid palladium catalyst under correlated reactive conditions of temperature and pressure which thermodynamically favor the formation of methanol relative to hydrocarbons, such as, methane. The selectivity of the reaction to methanol is generally at least 95%, and more typically about 99%.

Though the amount of methanol produced is significantly greater than the other oxygenated organic components, large scale production by this process will provide significant production of such other oxygenated organic compounds.

The reaction temperature markedly affects the productivity of the reaction with regard to methanol formation. Thus, an increase in reaction temperature results in an increased conversion to methanol with the proviso that the reaction pressure is correspondingly increased to avoid thermodynamic limitations. Increased pressure has relatively little affect on the productivity of the reaction but does affect product distribution. Thus, for example, at increased pressures, there is an increased proportion of ethylene glycol in the product mixture. For purposes of economy, the reaction pressure is preferably within the range of 150-3,000 psia although a reaction pressure of from about 150-20,000 psia is generally suitable.

The palladium metal catalyst of the invention can be employed alone in a fine dispersion or slurried in a high boiling point solvent, or alternatively, supported upon an inert carrier. The preferred mode of operation is to support the palladium catalyst on a high surface area support. Silica gel is the preferred catalyst base with alpha alumina and gamma alumina being less desirable. When used in conjunction with a support, the palladium catalyst defined by the invention is restricted to those supports which are catalytically inert with regard to promoting methanol formation from synthesis gas. Thus, the invention is predicated on the discovery that palladium metal is an active catalyst for selectively forming hydroxylated products containing 1-2 carbon atoms. Accordingly, the invention is directed toward the use of palladium as a catalyst in its own right and not in its heretofore known capacity as a dopant in conjunction with known methanol catalysts such as mixed oxides of zinc, chromium and copper.

The operable space velocities in the flow reactor may vary from about $10^2$ to $10^5$ per hour; space velocity being defined as volumes of reactant gas at 0° C. and 760 mm. mercury pressure, per volume of catalyst, per hour. Generally, the higher the space velocity, the more economical the overall reaction, although at excessively high space velocities the productivity of the reaction is adversely affected.

The ratio of hydrogen to carbon monoxide in the synthesis gas may vary extensively from about 10:1 to 1:10. The preferred hydrogen to carbon monoxide ratio is within the range of at least 1:1 to 5:1; a ratio of about 2:1 being most preferred. Increasing the percentage of hydrogen relative to carbon monoxide in the gas mixture increases the rate of the reaction, but adversely affects the economics of the overall process.

Palladium may be deposited onto the catalyst base or support by any of the commonly accepted techniques for catalyst preparation, such as, for example, impregnation from a solution containing palladium salt or ion exchange. Typically, a silica or gamma alumina support is impregnated with an aqueous solution of palladium chloride and hydrochloric acid, dried at 150° C., activated in air at 400° C., and thereafter reduced in hydrogen at 500° C. The preferred palladium concentration is from about 2-5%, by weight, of the catalyst support. However, a palladium concentration in the range of from about 0.1-20% is also suitable for the reaction.

Table I below summarizes the results of experiments conducted with supported palladium catalysts wherein the variables studied include reaction temperature, pressure, catalyst support, space velocity and feed composition. The quantity of products produced by the synthesis gas reaction are expressed in terms of mole/liter of catalyst/hour, based on 30 cc. of catalyst. No methane or higher molecular weight hydrocarbons were observed in the exit gases.

All of the catalysts tested with the exception of test number 13 were prepared in accordance with the following general sequence of steps: impregnation with $PdCl_2$ in $HCl-H_2O$; drying at 150° C.; activation in air at 400° C.; and reduction in hydrogen at 500° C.

A detailed description of the preparation of the preferred catalyst supported on silica is provided below.

CATALYST PREPARATION 200g of Davison TM Grade 57 silica (surface area: ~250 m$^2$/g) was impregnated with a 200-250 cc solution of 50% $H_2O$ and 50% conc. HCl which contained 16.7g of $PdCl_2$ (10gPd). The excess liquid phase was removed under vacuum with agitation at approximately 40° C. The material was futher vacuum dried at 150° C. for 2-3 hours without agitation. Subsequently, the catalyst was calcined in air for 1 hour at 300° C. and then at 400° C. for 2-3 hours. Following the air activation the sample was evacuated at room temperature and filled with argon. Finally, $H_2$ was carefully introduced to the catalyst as the temperature was raised to 300° C. The material was heated at 300° C. in $H_2$ for approximately 2 hours and then at 500° C. in $H_2$ for 2-3 hours. The sample was evacuated while hot and allowed to cool in vacuum. The finished catalyst was characterized as follows: surface area = 264 ± 3 m$^2$/g, Pd = 4.7% ± 0.2%, Cl = 0.06% ± 0.01% and an approximate Pd crystallite size of 55-60 A°.

The chemical analysis of Davison TM Grade 57 silica on a dry basis is as follows:

Silica as $SiO_2$ — 99.7%
Iron as $Fe_2O_3$ — 0.03%
Aluminum as $Al_2O_3$ — 0.10%
Titanium as $TiO_2$ — 0.04%
Calcium as CaO — 0.03%
Sodium as $Na_2O$ — 0.04%
Zirconium as $Zr_2O$ — 0.01%
Trace Elements — 0.03%

DESCRIPTION OF EXPERIMENTAL PROCEDURE 30 cc. of catalyst was charged into a tubular flow reactor (7/16 inches I.D.) which was thereafter flushed with hydrogen at 275° C. and at a pressure of 1500 psi for a period of 16 hours. The reactor was then flushed with nitrogen, adjusted to the desired temperature, and pressurized with synthesis gas of the specified composition. Flow was then established at the desired temperature, pressure, and flow rate for either a 2 or 4 hour period. Liquid products formed during the tests were collected in a water-containing, water-cooled condenser maintained at 1500 psi, and thereafter analyzed by gas chromatographic analysis. Gaseous products were analyzed by on-line gas chromatographic analysis. No water-insoluble liquid products were observed. Results of the tests are shown in Table I.

TABLE I

| | | | | | | | Productivity (mol l$^{-1}$ hr$^{-1}$) | | |
|---|---|---|---|---|---|---|---|---|---|
| | | Temp. | Press. | SV | CO:H$_2$ | Run time | | | |
| Test No. | Catalyst | (° C) | (psi) | (hr$^{-1}$) | Ratio | (hrs) | CH$_3$OH | HCO$_2$CH$_3$ | HOCH$_2$CH$_2$OH Other$^a$ |
| 1 | 4.6% Pd/SiO$_2$ | 275 | 16,000 | 3300 | 30:70 | 4 | 5.8 | 0.11 | 0.0023 |
| 2 | 4.6% Pd/SiO$_2$ | 275 | 16,000 | 3300 | 90:10 | 4 | 1.6 | 0.027 | 0.0010 |

TABLE I-continued

CONVERSION OF SYNTHESIS GAS OVER Pd CATALYSTS

| Test No. | Catalyst | Temp. (°C) | Press. (psi) | SV (hr$^{-1}$) | CO:H$_2$ Ratio | Run time (hrs) | Productivity (mol l$^{-1}$ hr$^{-1}$) | | | |
|---|---|---|---|---|---|---|---|---|---|---|
| | | | | | | | CH$_3$OH | HCO$_2$CH$_3$ | HOCH$_2$CH$_2$OH | Other[a] |
| 3 | 4.8% Pd/γ-Al$_2$O$_3$ | 275 | 16,000 | 3300 | 30:70 | 4 | 3.3 | 0.18 | trace | |
| 4 | 4.6% Pd/SiO$_2$ | 275 | 16,000 | 3300 | 30:70 | 4 | 4.5 | 0.083 | 0.0023 | [b] |
| 5 | 4.6% Pd/SiO$_2$ | 275 | 8,000 | 3300 | 30:70 | 4 | 3.9 | 0.048 | 0.0013 | [c] |
| 6 | 4.6% Pd/SiO$_2$ | 325 | 8,000 | 3300 | 30:70 | 4 | 15.2 | 0.27 | 0.0028 | CH$_3$CH$_2$OH 0.005 |
| 7 | 4.6% Pd/SiO$_2$ | 325 | 4,000 | 3300 | 30:70 | 4 | 9.7 | 0.12 | 0.0018 | CH$_3$CH$_2$OH 0.004 |
| 8 | 4.6% Pd/SiO$_2$ | 350 | 1,500 | 3300 | 30:70 | 4 | 7.1 | 0.03 | 0.0011 | CH$_3$CH$_2$OH 0.010 |
| 9 | 4.6% Pd/SiO$_2$ | 325 | 150 | 3300 | 30:70 | 4 | 0.48 | trace | trace | |
| 10 | 4.6% Pd/SiO$_2$ | 275 | 8,000 | 3300 | 30:70 | 2 | 4.4 | 0.048 | 0.0011 | |
| 11 | 0.5% Pd/SiO$_2$ | 275 | 8,000 | 3300 | 30:70 | 2 | 0.13 | trace | trace | |
| 12 | 4.5% Pd/C | 275 | 8,000 | 3300 | 30:70 | 2 | 0.05 | 0.007 | — | |
| 13 | 0.77% Pd/SiO$_2$ | 275 | 8,000 | 3300 | 30:70 | 2 | 0.06 | 0.003 | — | |
| 14 | 4.6% Pd/SiO$_2$ | 260 | 750 | 10,000 | 30:70 | 4 | 0.48 | — | trace | |
| 15 | 4.6% Pd/SiO$_2$ | 330 | 750 | 6700 | 30:70 | 4 | 2.5 | 0.0025 | trace | |

FOOTNOTES FOR TABLE 1

[a] Entries in this column represent cases where certain specific trace products were quantified; absence of any entry does not imply their absence.
[b] Other diols detected were 1,2-propanediol (~2/3 of quantity of ethylene glycol), 2,3-butanediols (~1/2 of quantity of ethylene glycol), and 1,2-butanediol (<1/10 of quantity of ethylene glycol); these products were observed in all runs at ≧4000 psi.
[c] 1,2-Propanediol was ~1/4 of ethylene glycol; 2,3-butanediols ~1/4 of ethylene glycol; 1,2-butanediol ~1/20 of ethylene glycol.

What is claimed is:

1. A heterogeneous catalytic process for selectively producing hydroxylated hydrocarbons containing from 1-2 carbon atoms from a gaseous mixture containing carbon monoxide and hydrogen which comprises contacting said gaseous mixture with a catalyst consisting essentially of palladium at a reaction temperature of from about 200° C. to about 400° C. and a reaction pressure of from about 150 to about 20,000 psia, the reaction pressure being correspondingly increased as reaction temperature is increased such that hydroxylated organic compounds are selectively produced in quantities greater than about 90%, by weight, of the total product mixture while substantially avoiding the concomitant formation of methane or higher molecular weight hydrocarbons.

2. The process of claim 1 wherein the temperature of the reaction is from about 260° to about 350° C. and the reaction pressure is from about 150 to about 3,000 psia.

3. The process of claim 1 wherein said palladium catalyst is supported on silica gel.

4. The process of claim 1 wherein the palladium concentration on the catalyst support is in the range of from about 2-5%, by weight, of the catalyst support.

5. The process of claim 1 wherein said synthesis gas is present in a ratio of hydrogen to carbon monoxide of from about 1:1 to 5:1.

* * * * *